United States Patent [19]

Alexander

[11] Patent Number: 5,306,251
[45] Date of Patent: Apr. 26, 1994

[54] DEVICE FOR INJECTING A FLUID OR INSERTING AN OBJECT BENEATH THE SKIN OF AN ANIMAL

[76] Inventor: Nicholas J. Alexander, Drayton House Farm, Drayton St., Leonard, Wallingford, Oxon, OX10 8BG, United Kingdom

[21] Appl. No.: 930,505
[22] PCT Filed: Mar. 27, 1991
[86] PCT No.: PCT/GB91/00461
  § 371 Date: Sep. 29, 1992
  § 102(e) Date: Sep. 29, 1992
[87] PCT Pub. No.: WO91/15165
  PCT Pub. Date: Oct. 17, 1991

[30] Foreign Application Priority Data
Mar. 30, 1990 [GB] United Kingdom ............... 9007207

[51] Int. Cl.$^5$ .................................. A61M 5/20
[52] U.S. Cl. ........................... 604/130; 604/137
[58] Field of Search .............. 604/130, 131, 137

[56] References Cited

U.S. PATENT DOCUMENTS

| | | | |
|---|---|---|---|
| 2,620,190 | 12/1952 | Bean | 604/130 |
| 3,214,067 | 10/1965 | Linington | 604/130 |
| 3,809,083 | 5/1974 | Westergaard . | |
| 3,837,284 | 9/1974 | Waldeisen | 604/130 |
| 4,103,893 | 8/1978 | Walker | 604/130 |
| 4,106,770 | 8/1978 | Gray | 604/130 |
| 4,121,586 | 10/1978 | Lawrence et al. | 604/130 |
| 4,578,064 | 3/1986 | Sarnoff et al. | 604/137 |
| 4,726,594 | 2/1988 | Benke | 604/130 |
| 4,735,611 | 4/1988 | Anderson et al. | 604/130 |
| 4,863,428 | 9/1989 | Chevalier | 604/130 |

FOREIGN PATENT DOCUMENTS

| | | | |
|---|---|---|---|
| 2477007 | 9/1981 | France | A61D 7/00 |
| 1366039 | 9/1974 | United Kingdom | F42B 13/54 |

Primary Examiner—Paul J. Hirsch
Attorney, Agent, or Firm—Webb, Burden, Ziesenheim & Webb

[57] ABSTRACT

A hand held device for injecting a fluid (such as a vaccine) or an object (such as a transponder) beneath the skin of an animal, the device comprising a mounting (2) for receiving a conventional hypodermic syringe (5,6,7), a weight (7) (which may be part of the plunger fitted within the syringe) for acting on the plunger (7) of the syringe and a slapping plate (3), being arranged so that when the device is swung into contact with an animal so the needle (6) of the hypodermic syringe pierces the animal's skin and the device is brought to a sudden halt as the plate (3) slaps against the animal, the momentum of the weight (7) acts to push the plunger (7) into the syringe and so propels the fluid or object held therein into the animal.

18 Claims, 9 Drawing Sheets

DEVICE FOR INJECTING A FLUID OR INSERTING AN OBJECT BENEATH THE SKIN OF AN ANIMAL

BACKGROUND OF THE INVENTION

1. Field of the Invention

This invention relates to a device for injecting a fluid or inserting an object beneath the skin of an animal.

2. Prior Art

There are a number of devices available for injecting livestock, for instance with a vitamin solution or other medication, but these suffer from a number of disadvantages.

The simplest device is a hand-held syringe. There are also hand-held injection guns which have a needle for inserting into an animal and a lever or trigger mechanism which is squeezed to inject fluid into the animal. With these devices, it is necessary to get close to the animal to be injected, to push the needle into the animal and then depress the plunger /r squeeze the trigger to inject the animal. In practice, these devices are difficult to use with un-restrained livestock, since the animals tend to move away and a certain degree of skill is required to carry out quickly the two actions of inserting the needle and then depressing the plunger (or squeezing the trigger) to inject the animal. Often the animal may move when the needle is inserted before the plunger can be depressed, or the animal moves before the needle is inserted and fluid is wasted as the plunger is inadvertently depressed. There is also considerable danger that the operator will accidentally inject himself if he misses an animal as it moves past his legs.

A further type of arrangement is described in U.S. Pat. No. 3,809,083. This comprises a syringe carried on the end of a pole together with a spring-loaded mechanism. When the needle is jabbed into an animal the spring-loaded mechanism is automatically triggered to discharge the syringe. The spring-loaded mechanism is complicated and requires many moving parts and the device can be inconvenient to use, especially when the animal is close to the person operating the device.

Dart guns may also be used to fire a dart containing the required fluid into the animal. However, these require skill in aiming and hitting the chosen animal, are relatively slow when many animals have to be injected, and require expensive equipment and may require a gun licence to operate.

Other devices are available for tattooing or marking an animal. These comprise a tattoo head (made up of a plurality of small needles) or a stamp, mounted on the end of an arm or handle. This type of device can be swung onto or pushed against the skin of an animal to provide the required marking. These devices are, however, limited to surface marking and are unable to inject anything beneath the skin.

SUMMARY OF THE INVENTION

The present invention aims to provide a device for injecting fluid or inserting an object beneath the skin of an animal which avoids some of the disadvantages of known devices and which is easier to use.

According to the present invention, there is provided a hand held device for injecting a fluid or inserting an object beneath the skin of an animal comprising: holding means for holding the fluid to be injected or object to be inserted into the animal; piercing means for piercing the animal's skin and drive means arranged to act automatically when the device is moved towards the animal and is brought to a sudden halt on engagement therewith after piercing the animal's skin, characterised in that the drive means comprises a weight arranged so that when the device is brought to a sudden halt on engaging the animal the momentum of the weight is used to propel the fluid or object through the piercing means into the animal.

Preferred features of the invention will be apparent from the following description and from the subsidiary claims of the specification.

BRIEF DESCRIPTION OF DRAWINGS

The invention will now be further described, merely by way of example, with reference to the accompanying drawings, in which.

DESCRIPTION OF THE PREFERRED EMBODIMENTS

Figure 1:
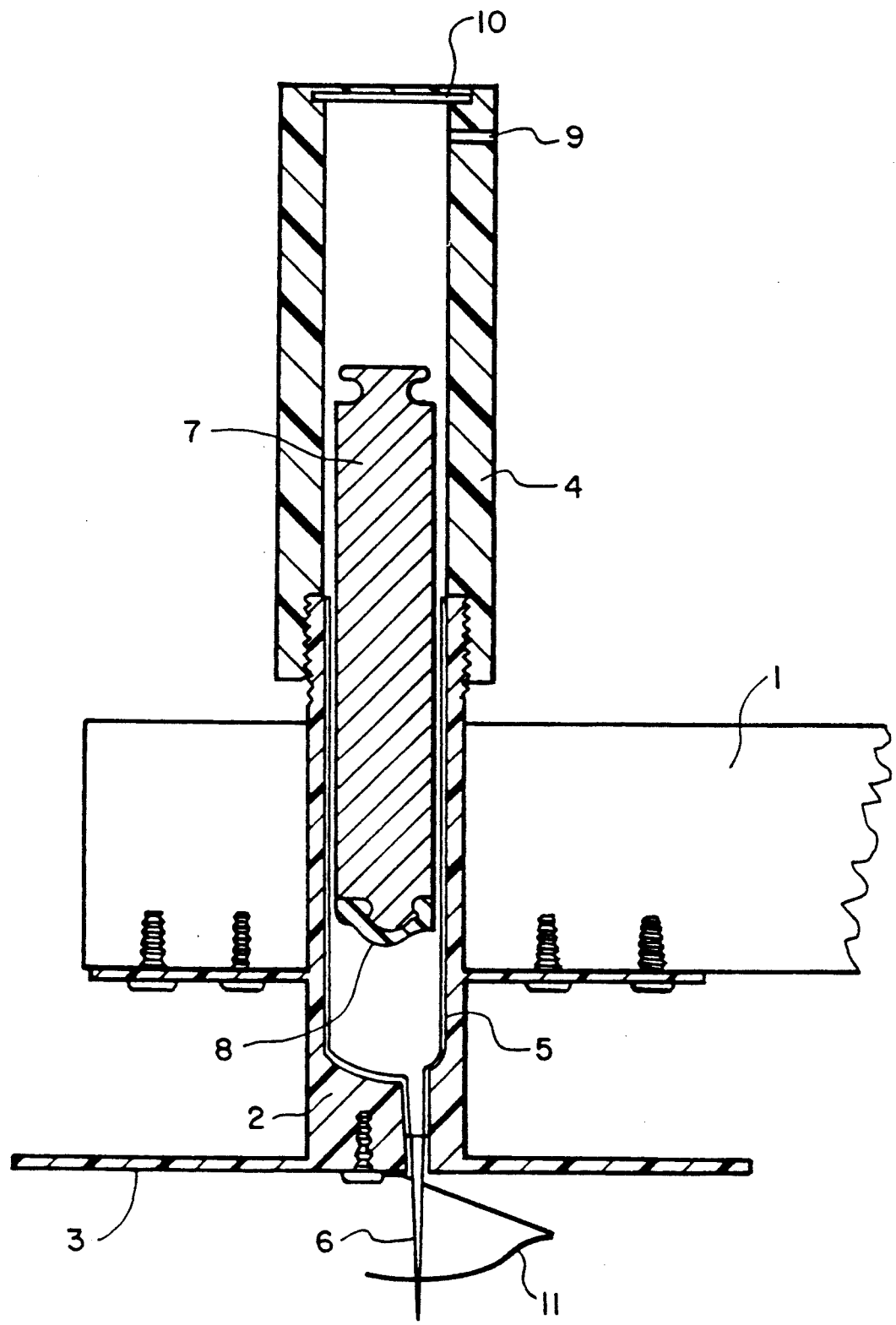
FIG. 1 is a sectional, side view of a first embodiment of a device according to the invention.

The device shown in FIG. 1 comprises a handle 1, a syringe mounting 2 secured thereto, a slapping plate 3 and a cover 4 attached to the syringe mounting 2. Within the syringe mounting is a conventional disposable syringe 5 having a conventional hypodermic needle 6 attached thereto which projects through the slapping plate 3. A plunger 7 in the form of a weight with a conventional rubber end piece 8 attached thereto is fitted within the syringe 5.

To prepare the device for use, the plunger 7 is pushed into a syringe 5 and a needle 6 attached to the syringe 5. The syringe 5 is then filled with the required quantity of fluid, e.g. a penicillin vaccine for sows, from a bottle in the conventional manner by inserting the needle 6 through a seal on the bottle and withdrawing the plunger 7 to draw the required quantity of fluid into the syringe 5. The syringe 5 is then fitted into the mounting 2 and the cover 4 secured to the mounting 2.

The device may then be used to inject an animal by holding the handle 1 and swinging the device against the animal, e.g. in the region of its neck, so the needle 6 pierces the animal's skin and the plate 3 slaps the animal. As the device is brought to an abrupt halt on engagement of the plate 3 with the animal, the heavy plunger 7 continues moving and its momentum is sufficient to push the plunger 7 into the syringe 5 so as to propel the fluid therein through the needle 6 and into the animal.

The momentum of the plunger 7 thus automatically injects the animal once the needle 6 has passed through its skin without any further action required by the operator. All the operator has to do is to swing or slap the device against the animal and in this single action the skin of the animal is pierced and the fluid is injected into the animal. Very little skill is therefore required to use the device and the animal is injected before it has a chance to move away. If the device is swung and misses the animal, no fluid is ejected (unless some other object is hit) so accidental loss of fluid is reduced.

The handle 1 may be made of any conventional material of suitable strength, e.g. wood, plastics or metal. It may typically be about 40 cm in length so the device can be used to inject an animal at a distance of 1 m or more from the operator. However, other length handles may be used if desired.

The syringe mounting 2 may typically be formed or metal, e.g. stainless steel, or a plastics moulding and secured to the end of the handle 1, e.g. by screws as shown in FIG. 1.

The cover 4 may be of similar material to the mounting 2 and is preferably provided with a hole 9 near its outer end to prevent movement of the plunger 7 being impeded by suction inside the cover 4. If the cover 4 is formed of plastics material, the top is preferably provided with a reinforcement 10 to reduce the danger of the plunger 7 damaging the cover 4 when the device is swung backwards to withdraw the plunger 7 from the syringe 5 and so move it back to its original position. The cover 4 may be secured to the mounting 2 by means of a screw thread or some form of clip.

The syringe 5 and needle 6 may be of any conventional design and the syringe mounting 2 is preferably designed to receive a variety of different types and sizes of syringe. 2.5, 5, 10 and 20 ml syringes may typically be used in this type of device, although the smaller the syringe the easier it is to ensure the entire contents are injected into the animal. The weight 7 is formed of a heavy material such as lead or steel and fitted with a rubber or plastics end piece 8 which is a close sliding fit within the syringe 5. The end piece of a conventional, lightweight plunger provided with the syringe 5 may be removed from the plunger and fitted instead to the weight 7 to form the end piece 8.

In an alternative arrangement (such as shown in FIGS. 8 to 11 described below) the conventional lightweight plunger provided with the syringe 5 may be used in the syringe 5 and the weight 7 arranged to act upon this plunger.

Figure 2:
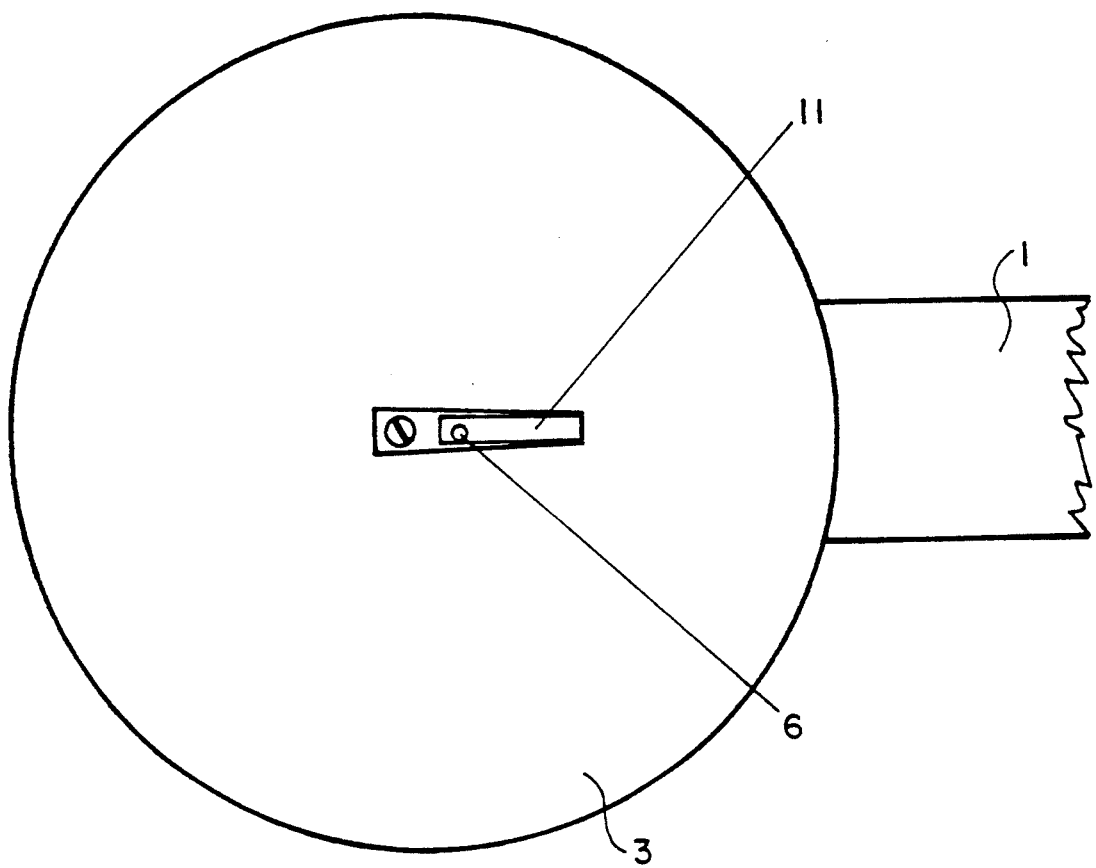
FIG. 2 is a view from beneath the device shown in FIG. 1.

As shown in FIGS. 1 and 2, the slapping plate 3 preferably comprises a circular plate secured to or forming part of the syringe mounting 2. The needle 6 projects from the centre of the plate 3 and passes through holes in a leaf spring 11 secured to the centre of the plate 3. The leaf spring 11 is compressed when the device engages an animal and the needle 6 pierces the animal's skin and assists in withdrawing the needle after the animal has been injected. The spring 11 also assists in ensuring the needle 6 pierces the animal at right angles to its skin. Other resilient means may, of course, be used in place of the leaf spring 11.

In a modification of the device (not shown), a reservoir may be mounted on the device, e.g. on the handle adjacent the mounting 2, containing fluid to re-charge the syringe 5 between injections. A small tube may lead from the reservoir to the syringe 5 so fluid may be transferred to the syringe by squeezing the reservoir.

Alternatively, the device may be arranged so that as it is swung backwards away from an animal that has been injected ready to slap or hit another animal, the heavy plunger 7 moves backwards to its original position within the cover 4 and so withdraws from the syringe 5, whereby fluid is automatically sucked from the reservoir into the syringe 5.

Figure 3:
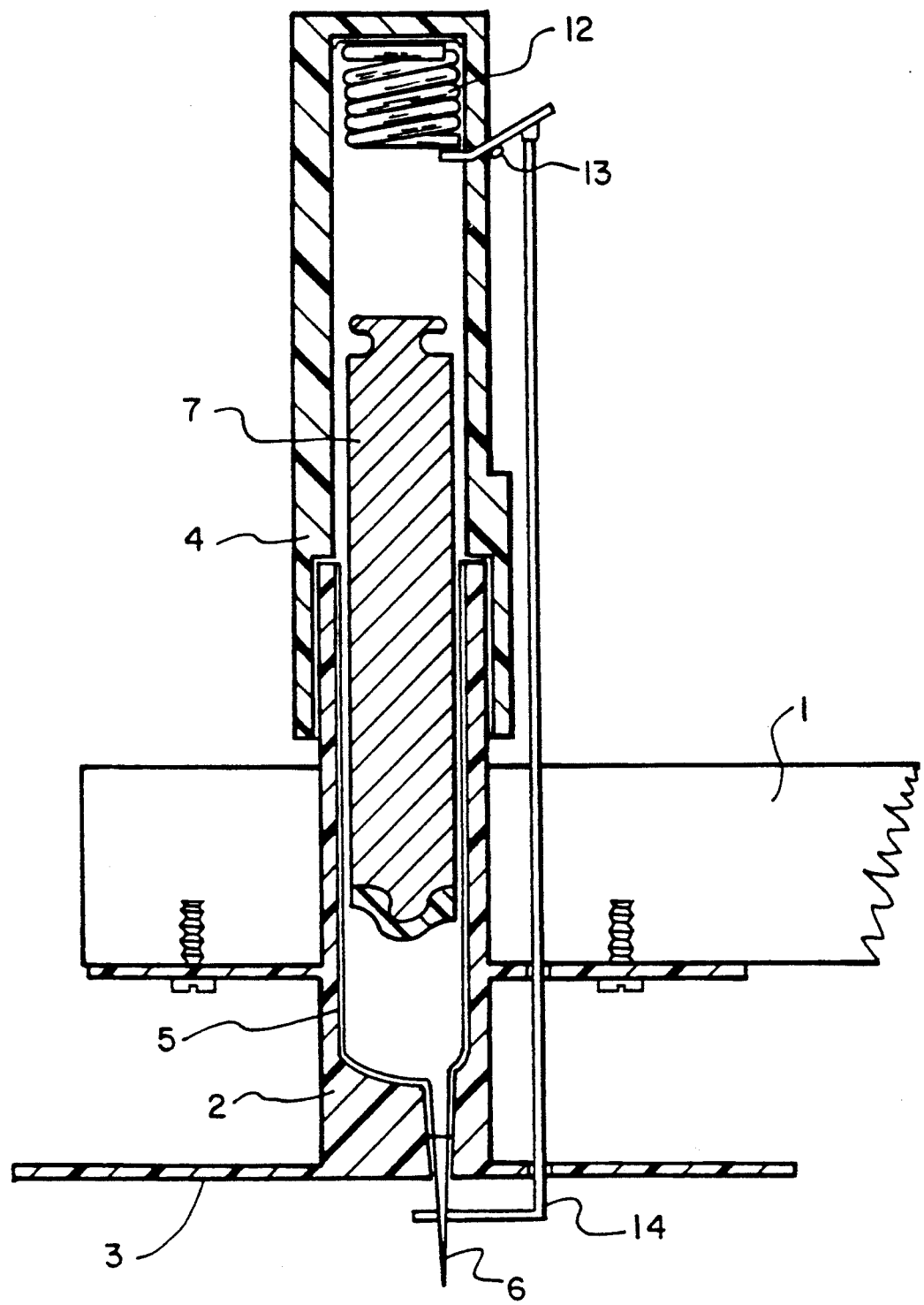
FIG. 3 is a sectional, side view of a second embodiment of a device according to the invention.

FIG. 3 shows a device similar to that shown in FIGS. 1 and 2 in which the plunger 7 is also spring assisted. A spring 12 is provided within the cover 4 and a release mechanism 13 is arranged to release the spring when the device is brought into contact with the animal. The release mechanism comprises an actuating rod 14 which passes through the plate 3 so it is actuated by engagement with the animal when the needle 6 has pierced the animal skin. When the spring 12 is released, it acts upon the plunger 7 and assists in driving it into the syringe 5 and thus to propel fluid through the needle 6.

A wide variety of other mechanisms may be used to release the spring at the appropriate time in place of that shown in FIG. 3.

Figure 4:
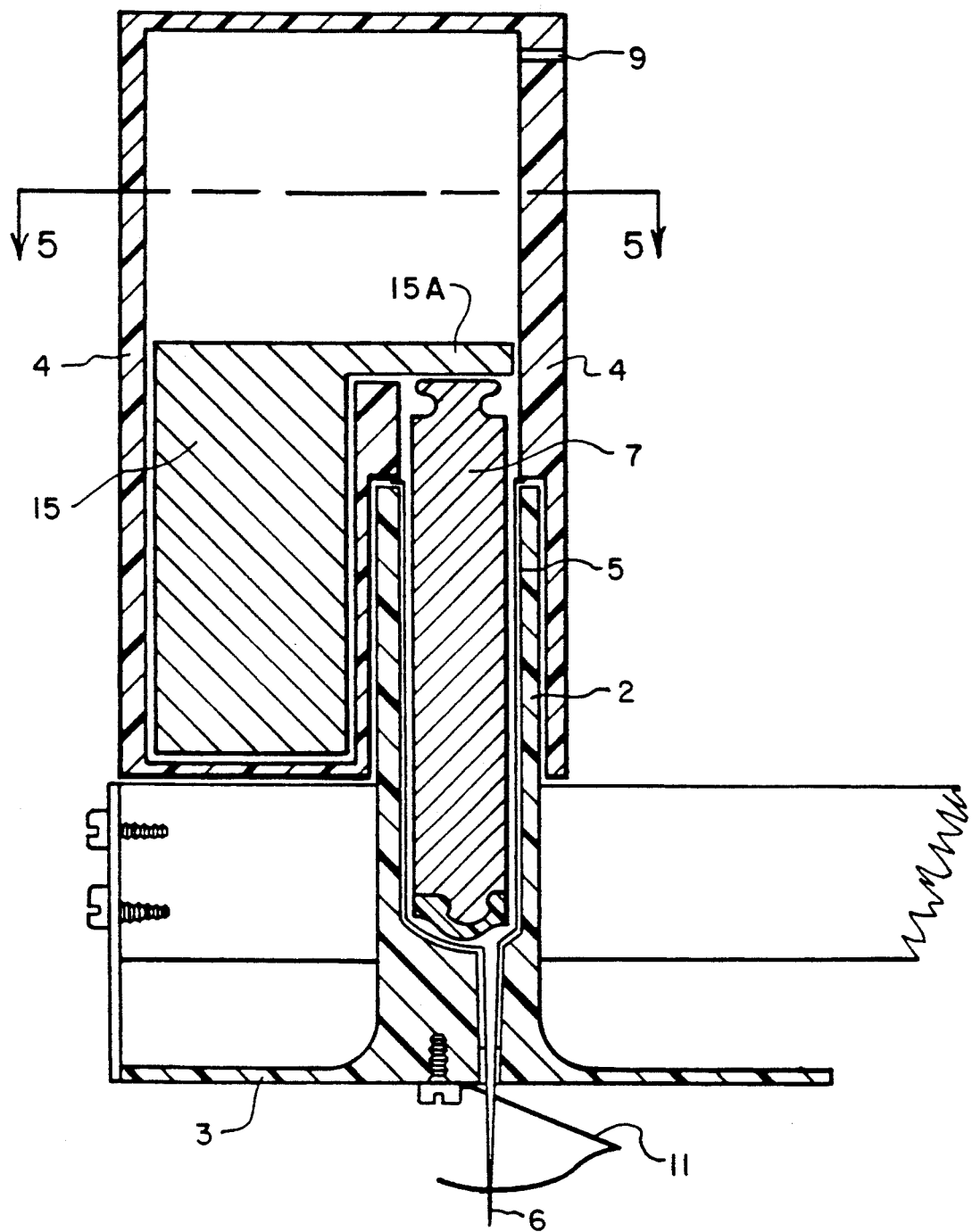
FIG. 4 is a sectional, side view of a third embodiment of a device according to the invention.
Figure 5:
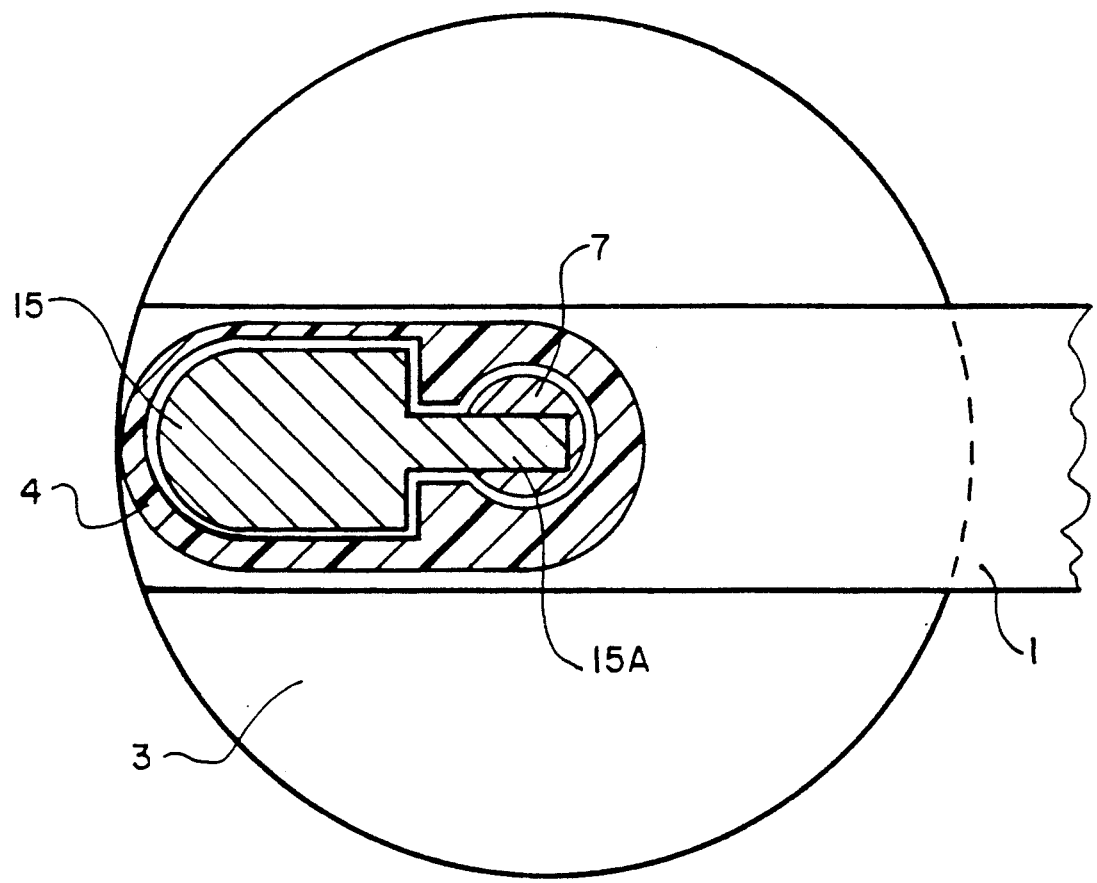
FIG. 5 is a sectional, plan view along line a—a of the device shown in FIG. 4.

FIGS. 4 and 5 show a further embodiment of the device in which a second weight 15 is provided to assist in driving the plunger 7 into the syringe 5. The second weight 15 may be of similar size or larger than the heavy plunger 5 and is slidably mounted in an extended portion of the cover 4 adjacent to the syringe 5. The second weight is provided with an extension 15A which is arranged to act upon the end of the plunger 5.

Due to the increased momentum of the combined weights 7 and 15, this arrangement is suitable for injecting larger quantities of fluid into an animal. The arrangement shown in FIG. 1 may, for instance, be used to inject up to about 20 ml of fluid. The arrangement shown in FIG. 4 may, however, be used to inject larger quantities of fluid, e.g. 30 or 40 ml.

Figure 6:
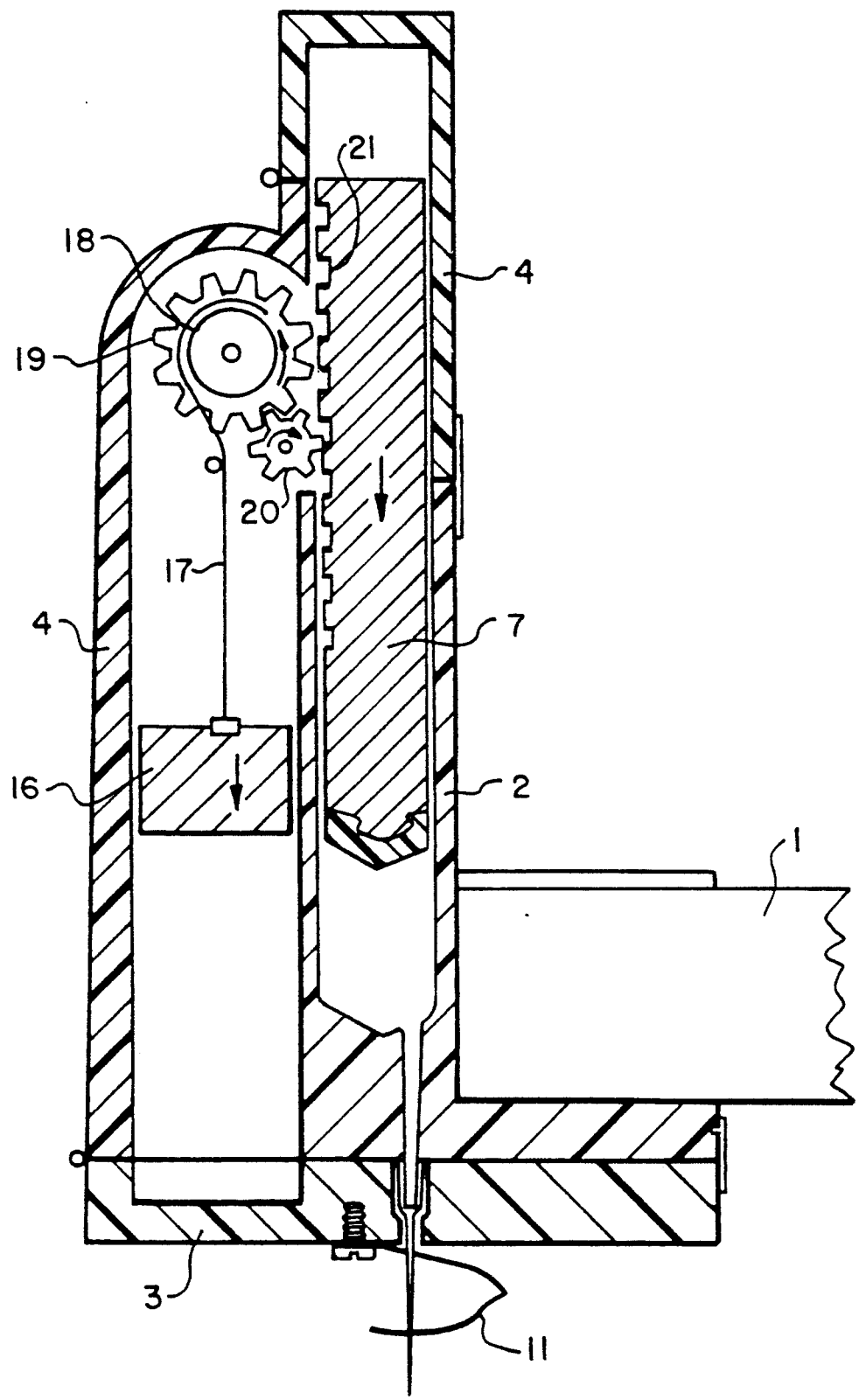
FIG. 6 is a sectional, side view of a fourth embodiment of a device according to the invention.

FIG. 6 shows another embodiment of the device for injecting larger quantities of fluid. In this case, a second weight 16 is slidably mounted in an extended portion of the cover 4. The cover 4 extends past the end of the handle 1 and the bottom of the cover 4 forms the slapping plate 3. As shown in the drawing, the top and bottom of the cover 4 may be hinged to provide access to the weights 7 and 16 as well as to the syringe 5. In this arrangement, the second weight 16 is able to travel a greater distance than the weight 15 shown in FIG. 4 and is arranged to act upon the plunger 7 via a ratchet and gear mechanism which is provided to compensate for the different distances travelled by the weight 16 and the heavy plunger 7. In the arrangement shown, the weight 16 is secured to a line 17 which is wound around a pulley 18. The pulley 18 turns a gear wheel 19 and this turns a smaller gear wheel 20 which engages ratchet teeth 21 provided along the side of the plunger 7.

A wide variety of other gear mechanisms for compensating for the different movements of the weights 7 and 16 may be used in place of that illustrated.

The device described above may be used to inject a wide variety of fluids, for example, vaccines, vitamin solutions and other medications.

Figure 7:
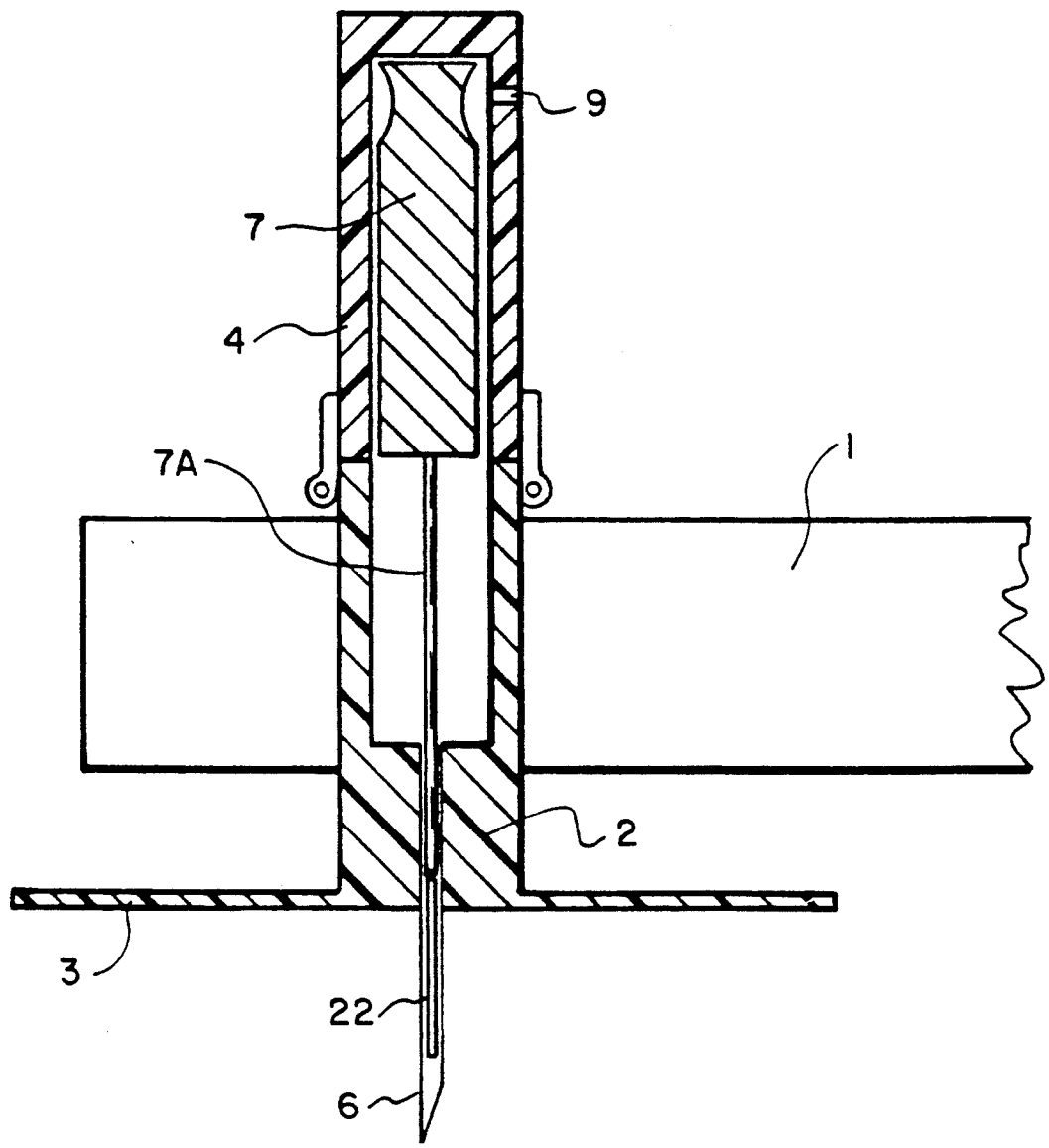
FIG. 7 is a sectional, side view of a fifth embodiment of a device according to the invention.

FIG. 7 shows a further arrangement in which the device is adapted to insert an object 22 under the skin of an animal rather than injecting a fluid. In this case, the needle 6 is modified to enable the object to be propelled through it and may thus require a bore of about 2 mm or more in diameter. The object 22 is mounted within the needle 6 as shown and propelled therethrough by means of a heavy plunger 7 provided with a rod 7A which engages the object 22 to push it through the needle 6 and into the animal as the plunger 7 moves into the mounting 2. The object 22 is thus propelled into the animal in a manner similar to the way fluid is propelled through the needle in the embodiments described above.

· In this way an object, such as an electronic transponder (which is typically about 1 cm long and 1 or 2 mm in diameter) may be inserted beneath the skin of an animal. Other objects which may be inserted in this way include other identification devices and capsules containing a fluid designed to be released into the animal over a period of time.

FIGS. 8 to 11 show another arrangement in which a weight 23 mounted on a hinged arm 24 provides the momentum to drive plunger 25 into a syringe 26 to propel fluid through a hypodermic needle 27 into an animal. As in the other embodiments, the syringe 26 is fitted within a mounting 2 provided with a slapping plate 3 and handle 1.

As the momentum is provided by the arm 24 and the weight 23, the plunger 25 may be of lightweight construction. The plastics plunger often supplied with a conventional syringe can be used although it may be preferable to substitute a stronger, metal form of plunger. In this case, the end piece 8 provided on the conventional plunger can be removed and fitted to the plunger used in its place.

The arm 24 is hinged to the handle 1 and carries a cover 4 and the weight 23. Within the cover 4, there is provided a coil spring 28 and a member 29 which is slidable within the cover against the action of the spring 28. The member 29 is preferably provided with a curved surface to engage the end of the plunger 25 so as to allow the relative movement therebetween.

Figure 8:
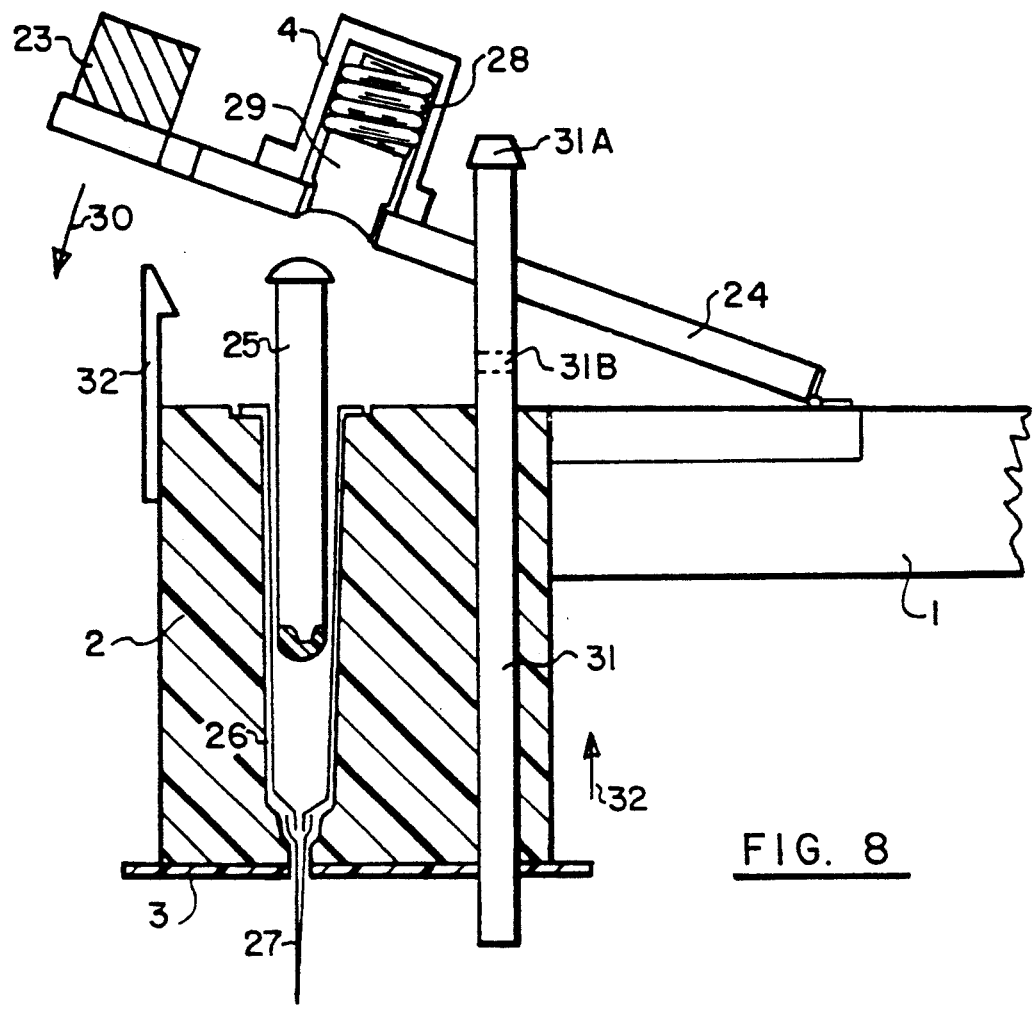
FIG. 8 is a sectional, side view of a sixth embodiment of a device according to the invention.
Figure 11:
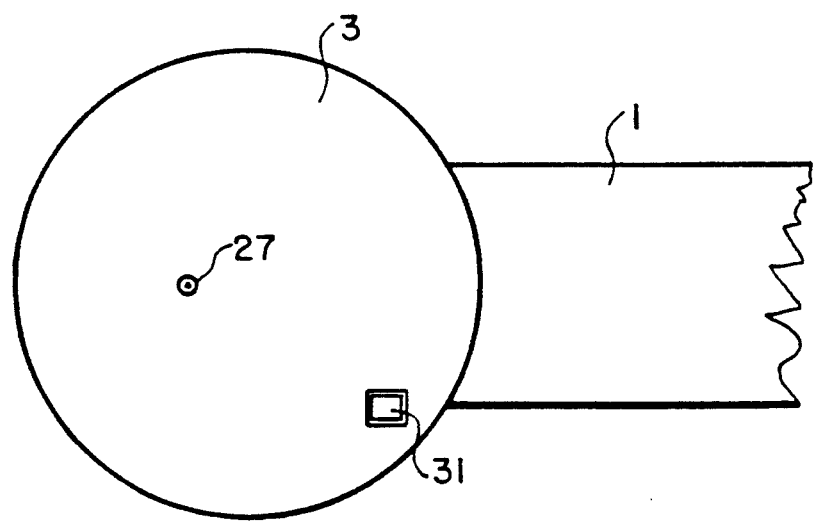
FIG. 11 is a view from beneath the device shown in FIG. 8.
Figure 10:
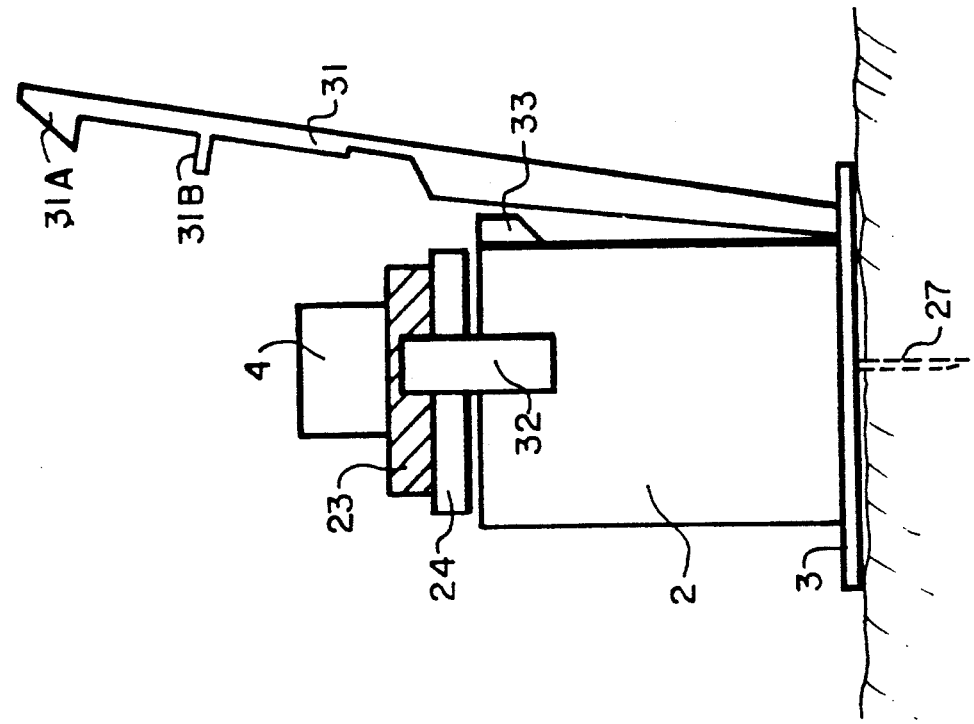
FIG. 9 and 10 are end views of the device shown in FIG. 8 showing the device before and after use.
Figure 9:
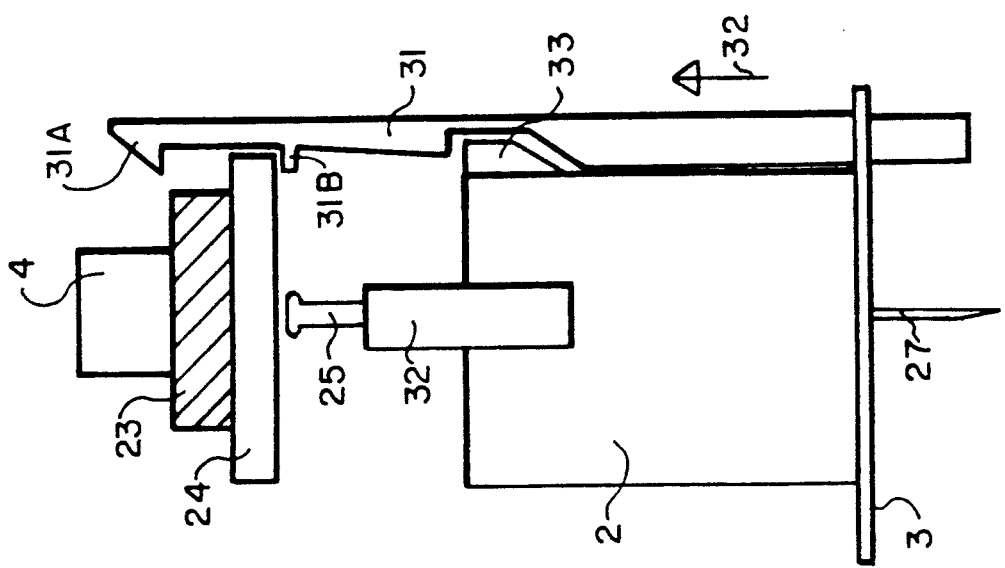

To use the device, the syringe 26 is first filled with the required fluid in the conventional manner and then fitted into the mounting 2. The arm 24 is then positioned as shown in FIGS. 8 and 9 with the member 29 resting on the end of the plunger 25. When the device is swung against an animal to be injected, and is brought to a sudden halt after the needle 27 has pierced the animal's skin and the slapping plate engages the animal, the momentum of the arm 24 and the weight 23 carried thereby causes the arm 24 to continue moving (as shown by arrow 30) to drive the plunger 25 into the syringe 26 until the arm 24 engages the top of the mounting 2 as shown in FIG. 10.

As the arm 24 moves in the direction of arrow 30, the member 29 begins pushing the plunger 25 into the syringe 26 but at the same time it compresses the spring 28 within the cover 24. When the arm 24 engages the mounting 2, the spring 28 expands to continue moving the member 29 so as to push the plunger 25 into the syringe 26 thereby completing the transfer of momentum from the arm 24 and weight 23 to the plunger 25. By this means the momentum of the arm 24 and weight 23 is transferred more smoothly to the plunger 25 and the fluid held within the syringe 26. Without the cushioning effect provided by the spring 28, there is a danger that momentum will be transferred so suddenly to the plunger 25 and the fluid within the syringe 26 as to cause the plunger 25 to break or the syringe 26 to burst as the fluid cannot escape sufficiently quickly through the fine bore of the needle 27.

To assist in easy operation of the device two catches 31 and 32 are provided on the outside of the mounting 2. The first catch 31 serves to hold the arm 24 in the raised position as shown in FIGS. 8 and 9 between two stops 31A and 31B provided at one end of the catch. The other end of the catch extends beyond the mounting 2 and slap plate 3 so that it engages the animal as the needle 27 pierces the animal's skin. This causes the catch 31 to slide against the side of the mounting 2 in the direction of arrow 32 whereby a cam surface 33 on the side of the mounting 2 forces the catch to move sideways to the position shown in FIG. 9 so that the stops 31A and 31B are moved out of engagement with the arm 24.

The catch 31 thus serves to hold the arm 24 in the raised position shown in FIG. 8 and prevents the arm swinging further away from the mounting 2 but is automatically disengaged from the arm 24 when the device is swung into contact with an animal.

The second catch 32 engages the arm 24 when it has moved into contact with the mounting 2 to prevent the arm 24 rebounding away from the mounting 2 as the device is brought to a sudden halt on engaging the animal.

Other mechanisms may, of course, be used to provide the functions of catches 31 and 32 as will be apparent to those skilled in the art.

The arrangement shown in FIGS. 8 to 11 may also be altered in other ways, for instance the cover 4 and/or arm 24 may be formed of a heavy material so a separate weight 23 is not required, the spring 28 may be replaced by other resilient means such as resilient foam or a sealed air chamber and the member 29 may take other forms and may be formed from an elastic membrane to provide the function of both the member 29 and the spring 28.

In a modification (not shown) of the device shown in FIGS. 8 to 11, the spring 28 may be arranged so that it can be pre-stressed and so assist further in pushing the plunger 25 into the syringe 26 and a simple trigger mechanism (such as that shown in FIG. 3) provided to automatically release the spring 28 at the appropriate time.

The devices described above are provided with a handle 1 so the device can be swung into contact with an animal. The device may also be arranged (particularly when only small quantities of fluid are to be injected) so that it can be held in the hand, e.g. in the palm of the hand with the cover 4 passing between the fingers. The device can thus be brought into engagement with the animal by moving the arm as if to strike or slap the animal. In each case, the action required by the operator is a simple natural movement of the arm to slap the animal with the device so the device can be easily used and requires little skill to operate.

It will be appreciated that in the arrangements described using a weight or other relatively heavy component of the device to drive the plunger into the syringe, the energy for this is derived from the momentum of the weight, i.e. the kinetic energy of the weight as the device is brought to a sudden halt as the slapping plate engages the animal is transferred to the plunger to propel the fluid or insert the object into the animal.

The devices described above provide a simple and inexpensive tool for injecting fluid or inserting objects under the skin of an animal. The injection occurs automatically once the animal's skin has been pierced, so only a single movement of the operator's arm is required to bring the device into contact with the animal and to inject the animal. This provides a significant advantage over prior art methods which require two separate movements—one to pierce the animal's skin and a second to depress a plunger of squeeze a trigger to inject the animal and so requires greater skill to operate. With the device described above, it is possible to inject the animal before it realises what is happening. Also, injection only occurs when the device is brought to a halt, or when the release mechanism is actuated, so fluid is not ejected until the skin of the animal has been pierced. The wastage of fluid can therefore be reduced. The device is particularly suitable for injecting unrestrained livestock but may also be used with animals held within a pen or crate.

Livestock can be injected easily and quickly using the device described above even when relatively large quantities of fluid need to be injected. The device is of a very simple and robust construction so is able to provide reliable and trouble-free operation. The syringes used may be of the conventional, disposable type and can be readily changed when the device is to be used for injecting a different fluid. This provides for hygienic operation and avoids problems with cross-contamination of fluids (which can arise for example with conventional injection guns).

INDUSTRIAL APPLICABILITY

The device described above can be manufactured and used by farmers and veterinary surgeons for injecting livestock and other animals.

I claim:

1. A hand-held device for injecting material beneath the skin of an animal comprising:
   holding means for holding the material to be injected into the animal;
   piercing means for piercing the animal's skin coupled to said holding means and configured to have the material pass therethrough;
   a plate coupled to said piercing means from which said piercing means projects; and
   momentum drive means coupled to said holding means for propelling the material from said holding means through said piercing means into the animal, said momentum drive means including at least one weight configured for movement relative to said holding means, wherein when said hand-held device is moved towards the animal and is brought to a sudden halt on engagement of said plate with the animal after said piercing means has pierced the animal's skin, the momentum of said weight is used to propel the material from said holding means through said piercing means into the animal.

2. The device as claimed in claim 1 in which said holding means comprises a removable syringe for holding a fluid to be injected into the animal, and said piercing means comprises a hypodermic needle attached to said syringe.

3. The device as claimed in claim 2 in which said weight is arranged to act on a plunger within said syringe, wherein when said hand-held device is brought to a sudden halt on engagement of said plate with the animal, the momentum of said weight drives said plunger into said syringe so the fluid therein is propelled through said needle into the animal.

4. The device as claimed in claim 3 wherein said weight is integral with said plunger which is fitted within said syringe.

5. The device as claimed in claim 3 further including a second weight slidably mounted within a chamber adjacent said syringe and configured to act on said weight wherein in operation the momentum of said weight and said second weight drives said plunger into said syringe.

6. The device as claimed in claim 5 further including a gearing mechanism positioned between said second weight and said weight wherein said gearing mechanism permits said second weight to travel a greater distance than said weight during operation.

7. The device as claimed in claim 3 further including a movable member pivotably attached to said holding means, wherein said weight is attached to said movable member such that when said hand-held device is brought to a sudden halt on engagement of said plate with the animal, said movable member continues moving providing for the transfer of the momentum of said weight to said plunger.

8. The device as claimed in claim 7 further including a second resilient means attached to said movable member configured to store at least a portion of the energy from the momentum of said weight as said device is brought to a sudden halt, wherein said second resilient means is configured to act on said plunger, such that the energy from the momentum of said weight is gradually transferred to said plunger.

9. The device as claimed in claim 7 further including restraining means for restraining movement of said movable member relative to said holding means.

10. The device as claimed in claim 2 wherein said drive means includes a first resilient means arranged to be stressed and then released when said hand-held device is brought into contact with the animal, wherein said first resilient means assists in driving a plunger into said syringe so the fluid therein is propelled through said needle into the animal.

11. The device as claimed in claim 10 further including a trigger means for releasing said first resilient means, said trigger means having a component which is actuated by engagement of said hand-held device with the animal.

12. The device as claimed in claim 2 further including a reservoir for holding sufficient fluid for several injections and transfer means for transferring the fluid from said reservoir to said syringe.

13. The device as claimed in claim 12 wherein said transfer means is actuated when said hand-held device is moved to return each said weight to its original position.

14. The device as claimed in claim 1 further including an auxiliary resilient means positioned on said plate adjacent said piercing means, wherein said auxiliary resilient means is configured to be compressed on engagement of said plate with the animal and thereby assists in withdrawing said piercing means after the animal has been injected.

15. The device as claimed in claim 1 wherein said hand-held device is configured to be held in the palm of the user.

16. The device as claimed in claim 1 further including an elongated handle coupled to said holding means.

17. The device as claimed in claim 1 wherein said material is a fluid for injecting into the animal.

18. The device as claimed in claim 1 wherein said material is an object to be inserted into the animal.

* * * * *